United States Patent [19]
Mikuni et al.

[11] Patent Number: 5,824,180
[45] Date of Patent: Oct. 20, 1998

[54] METHOD OF BONDING OR DECORATING ARTIFICIAL NAIL

[75] Inventors: Hiroyuki Mikuni; Yuko Nishiyama, both of Tokyo, Japan

[73] Assignee: Three Bond Co., Ltd., Tokyo, Japan

[21] Appl. No.: 741,117

[22] Filed: Oct. 30, 1996

Related U.S. Application Data

[63] Continuation-in-part of Ser. No. 730,025, Oct. 11, 1996.

[30] Foreign Application Priority Data

| Oct. 19, 1995 | [JP] | Japan | 7-296281 |
| Jan. 12, 1996 | [JP] | Japan | 8-022037 |

[51] Int. Cl.$^6$ .................................................. A45D 31/00
[52] U.S. Cl. .................................... 156/275.3; 156/275.5; 156/275.7; 156/332; 132/73; 424/61; 522/29
[58] Field of Search .............................. 156/272.2, 275.1, 156/275.7, 332, 275.3, 275.5; 424/61; 132/73; 522/29, 66, 170, 173; 585/419

[56] References Cited

U.S. PATENT DOCUMENTS

| 3,717,558 | 2/1973 | McGinniss | 522/27 |
| 4,596,260 | 6/1986 | Giuliano | 132/73 |
| 4,687,827 | 8/1987 | Russo | 427/340 |
| 4,818,325 | 4/1989 | Hiraiwa et al. | |
| 5,073,652 | 12/1991 | Katsuno | 585/419 |
| 5,389,700 | 2/1995 | Sasaki | |

FOREIGN PATENT DOCUMENTS

| 0447930 | 9/1991 | European Pat. Off. |
| 0573805 | 12/1993 | European Pat. Off. |

*Primary Examiner*—Michael W. Ball
*Assistant Examiner*—Michael A. Tolin
*Attorney, Agent, or Firm*—Sughrue, Mion, Zinn, Macpeak & Seas, PLLC

[57] ABSTRACT

A method of bonding an artificial nail to a nail with a photocurable cyanoacrylate adhesive or of decorating an artificial nail or a nail using the adhesive. The adhesive comprises (A) an cyanoacrylate monomer, (B) a catalyst selected from the group consisting of a metallocene compound comprising a transition metal of Group VIII of the periodic table and aromatic electron system ligands, and a mixed catalyst consisting of a combination of a cleavage-type photoinitiator and a metallocene compound comprising a transition metal of Group VIII of the periodic table and aromatic electron system ligands, an acetylacetonatoplatinum(II) complex, and a specific metal complex which releases a nucleophilic agent upon light irradiation. The curability of the adhesive of the present invention in the bonding of an artificial nail to a nail or in the bonding of a decorative article to a nail or artificial nail is improved in the case where the adhesive has flowed out of the bonding part or has been applied thickly so as to fill (build up) the recessed part of the joint, etc.

15 Claims, No Drawings

METHOD OF BONDING OR DECORATING ARTIFICIAL NAIL

CROSS-REFERENCE TO RELATED APPLICATION

This application is a continuation-in-part of corresponding U.S. application Ser. No. 08/730,025 filed Oct. 11, 1996.

FIELD OF THE INVENTION

α-Cyanoacrylate adhesives are used in many applications as cold-setting single-liquid type instantaneous adhesives, because they rapidly polymerize and cure by the action of a minute amount of the adsorption water present on adherend surfaces to extremely tenaciously bond the adherends to each other in a short time period. Among those applications are the bonding of artificial nails to nails and the bonding of various decorative articles to artificial nails.

BACKGROUND OF THE INVENTION

Various prior art techniques for the bonding of artificial nails to nails with an α-cyanoacrylate adhesive have been disclosed. For example, specific α-cyanoacrylate adhesive compositions for artificial-nail bonding are disclosed in JP-A-58-99908 and JP-A-58-103406. (The term "JP-A" as used herein means an "unexamined published Japanese patent application.") In JP-A-59-226077 is disclosed an α-cyanoacrylate adhesive composition for artificial-nail bonding which contains poly(vinyl acetate) having a weight-average molecular weight of 10,000 or higher. In JP-A-6-264034 is disclosed an α-cyanoacrylate adhesive composition for artificial-nail bonding which contains a halogenonitropropane. Further, an α-cyanoacrylate adhesive composition for artificial-nail bonding which contains a specific fluorinated alkyl acrylate or fluorinated alkyl methacrylate is disclosed in JP-A-7-70519.

There are several methods for the attachment of an artificial nail. A representative method comprises bonding an artificial nail to a nail, subsequently filling (building up) the recessed part of the joint between the nail and the artificial nail with a resin, smoothing the resin surface with a nail file or nail polisher, and then finishing the joint and the artificial nail by coating a nail lacquer or a resin. If desired, a decorative article is bonded to the surface of the artificial nail.

However, the α-cyanoacrylate adhesives have a drawback that the curing is very slow when the gap between adherends is wide, when the adhesive applied has overflown from the bonding part, or when the adhesive applied is not sandwiched between adherends as in coating. Because of this, the use of those α-cyanoacrylate adhesives is basically limited to the bonding of artificial nails to nails.

In the case where an α-cyanoacrylate adhesive is used for filling (building up) the recessed part of the joint between a nail and an artificial nail or as a finishing coating agent, the generally employed method for curing the adhesive is to use a primer or a curing accelerator. In attaching a decorative article to an artificial nail, it is difficult to apply the adhesive in a controlled amount so as to prevent the adhesive from flowing out of the bonding part because the decorative article is small. In this case also, when the adhesive which has flowed out is cured, a primer or a curing accelerator is used. However, such methods are disadvantageous not only in that the steps are troublesome, but also from the standpoint of working environment, for example, because the odor of the basic compound used as the main component of the primer or curing accelerator and the odor of the solvent make the user unpleasant.

There has hence been a desire for a cyanoacrylate adhesive which retains the excellent features of instantaneous adhesives, i.e., cold-setting and single-liquid type, and which is usable not only as an adhesive for bonding a nail to an artificial nail, but also as an improved filling (building up) material to be applied to the recessed part of the joint between the nail and the artificial nail, as a coating agent for finishing, or as an adhesive for bonding a decorative article to an artificial nail.

SUMMARY OF THE INVENTION

An object of the present invention is to provide a method of bonding an artificial nail to a nail with an adhesive or of decorating an artificial nail or a nail using an adhesive to overcome the above-described problems in the prior art.

To accomplish the above object, the problems described above were eliminated by bonding an artificial nail to a nail with a photocurable cyanoacrylate adhesive or by bonding a decorative article to an artificial nail with the adhesive.

The present inventors have found that the above object is achieved with the following embodiments:

(1) A method of bonding an artificial nail to a nail with an adhesive or of decorating an artificial nail or a nail using an adhesive, said adhesive being a photocurable cyanoacrylate adhesive.

(2) The method of bonding an artificial nail to a nail with an adhesive or of decorating an artificial nail or a nail using an adhesive according to the embodiment (1), which comprises applying a photocurable cyanoacrylate adhesive to a bonding surface of the nail or artificial nail or to a bonding surface of a decorative article or of the nail or artificial nail, subsequently superposing the adherends on each other, and then irradiating the superposed adherends with light to cure the adhesive and complete the bonding.

(3) The method of bonding an artificial nail to a nail with an adhesive or of decorating an artificial nail or a nail using an adhesive according to the embodiment (1) or (2), wherein the photocurable cyanoacrylate adhesive comprises:

(A) an α-cyanoacrylate and
(B) a metallocene compound comprising a transition metal of Group VIII of the periodic table and aromatic electron system ligands.

(4) The method of bonding an artificial nail to a nail with an adhesive or of decorating an artificial nail or a nail using an adhesive according to the embodiment (3), wherein each of the aromatic electron system ligands in the metallocene compound (B) is a π-arene, indenyl, or η-cyclopentadienyl.

(5) The method of bonding an artificial nail to a nail with an adhesive or of decorating an artificial nail or a nail using an adhesive according to the embodiment (3), wherein the metallocene compound (B) comprising a transition metal of Group VIII of the periodic table and aromatic electron system ligands is represented by the following formula (1):

(wherein M represents a transition metal of Group VIII of the periodic table; R represents a halogen atom, a hydrocarbon group having 1 to 20 carbon atoms, a halogenated hydrocarbon group having 1 to 20 carbon atoms, or a silicon-atom containing, oxygen-atom containing, sulfur-atom containing, or phosphorus-atom containing group having 1 to 20 carbon atoms, provided that the R's may be the same or different and may be crosslinked to each other; symbol a represents an integer of from 0 to 5; and the groups [$R_a$—Cp] (Cp represents η-cyclopentadienyl) may be the same or different).

(6) The method of bonding an artificial nail to a nail with an adhesive or of decorating an artificial nail or a nail using an adhesive according to the embodiment (3), wherein the transition metal of Group VIII of the periodic table in the metallocene compound (B) is a transition metal selected from the group consisting of iron, osmium, ruthenium, cobalt and nickel.

(7) The method of bonding an artificial nail to a nail with an adhesive or of decorating an artificial nail or a nail using an adhesive according to any of the embodiments (3) to (6), wherein the photocurable cyanoacrylate adhesive further comprises (C) a cleavage-type photoinitiator.

(8) The method of bonding an artificial nail to a nail with an adhesive or of decorating an artificial nail or a nail using an adhesive according to the embodiment (1) or (2), wherein the photocurable cyanoacrylate adhesive comprises:
  (A) an α-cyanoacrylate and
  (B) an acetylacetonatoplatinum(II) complex.

(9) The method of bonding an artificial nail to a nail with an adhesive or of decorating an artificial nail or a nail using an adhesive according to the embodiment (1) or (2), wherein the photocurable cyanoacrylate adhesive comprises:
  (A) an α-cyanoacrylate and
  (B) a metal complex which releases a nucleophilic agent upon light irradiation.

The photocurable cyanoacrylate adhesive composition for use in the present invention is generally obtained from a composition consisting mainly of an α-cyanoacrylate monomer represented by formula (2):

$$H_2C=C(CN)-COOR \qquad (2)$$

(wherein R represents an ester residue, examples of which include an alkyl group, a cycloalkyl group, an alkenyl group, a cycloalkenyl group, an alkynyl group, and an aryl group, and which usually has from 1 to 8 carbon atoms, although the number of carbon atoms thereof is not particularly limited; the ester residue may be a substituted hydrocarbon group such as an alkoxyalkyl group or a trialkylsilylalkyl group) by adding to the composition a catalyst capable of polymerizing and curing the α-cyanoacrylate monomer with the aid of light irradiation. Examples of the photocurable cyanoacrylate adhesive composition according to the present invention include the following compositions 1) to 4).

1) A cyanoacrylate adhesive composition comprising the following ingredients (A) and (B):
  (A) an α-cyanoacrylate and
  (B) a metallocene compound comprising a transition metal of Group VIII of the periodic table and aromatic electron system ligands.

2) A cyanoacrylate adhesive composition comprising the following ingredients (A) to (C):
  (A) an α-cyanoacrylate,
  (B) a metallocene compound comprising a transition metal of Group VIII of the periodic table and aromatic electron system ligands, and
  (C) a cleavage-type photoinitiator.

3) A cyanoacrylate adhesive composition comprising the following ingredients (A) and (B):
  (A) an α-cyanoacrylate and
  (B) an acetylacetonatoplatinum(II) complex.

4) A cyanoacrylate adhesive composition comprising the following ingredients (A) and (B):
  (A) an α-cyanoacrylate and
  (B) a specific metal complex which releases a nucleophilic agent upon light irradiation.

DETAILED DESCRIPTION OF THE INVENTION

The α-cyanoacrylate monomer contained in the photocurable cyanoacrylate adhesive composition for use in the present invention is then explained below in detail. The α-cyanoacrylate is a monomer represented by formula (2):

$$H_2C=C(CN)-COOR \qquad (2)$$

(wherein R represents an ester residue, examples of which include an alkyl group, a cycloalkyl group, an alkenyl group, a cycloalkenyl group, an alkynyl group, and an aryl group, and which usually has from 1 to 8 carbon atoms, although the number of carbon atoms thereof is not particularly limited; the ester residue may be a substituted hydrocarbon group such as an alkoxyalkyl group or a trialkylsilylalkyl group). Examples of the α-cyanoacrylate monomer include alkyl and cycloalkyl α-cyanoacrylates such as methyl α-cyanoacrylate, ethyl α-cyanoacrylate, propyl α-cyanoacrylate, butyl α-cyanoacrylate, and cyclohexyl α-cyanoacrylate; alkenyl and cycloalkenyl α-cyanoacrylates such as allyl α-cyanoacrylate, methallyl α-cyanoacrylate, and cyclohexenyl α-cyanoacrylate; alkynyl α-cyanoacrylates such as propargyl α-cyanoacrylate; aryl α-cyanoacrylates such as phenyl α-cyanoacrylate and tolyl α-cyanoacrylate; heteroatom-containing α-cyanoacrylates such as methoxyethyl α-cyanoacrylate, ethoxyethyl α-cyanoacrylate, and furfuryl α-cyanoacrylate; and silicon atom-containing α-cyanoacrylates such as trimethylsilylmethyl α-cyanoacrylate, trimethylsilylethyl α-cyanoacrylate, trimethylsilylpropyl α-cyanoacrylate, and dimethylvinylsilylmethyl α-cyanoacrylate.

Examples of catalysts usable for imparting photocurability to the α-cyanoacrylate monomer described above include:
(a) a metallocene compound comprising a transition metal of Group VIII of the periodic table and aromatic electron system ligands,
(b) a mixed catalyst consisting of a combination of a cleavage-type photoinitiator and a metallocene compound comprising a transition metal of Group VIII of the periodic table and aromatic electron system ligands,
(c) an acetylacetonatoplatinum(II) complex, and
(d) a specific metal complex which releases a nucleophilic agent upon light irradiation.

The above described (a) metallocene compounds comprising a transition metal of Group VIII of the periodic table and aromatic electron system ligands are represented by the following formula (1):

(In the formula, M represents a transition metal of Group VIII of the periodic table. R represents a halogen atom, a hydrocarbon group having 1 to 20 carbon atoms, a halogenated hydrocarbon group having 1 to 20 carbon atoms, or a silicon atom-containing, oxygen atom-containing, sulfur atom-containing, or phosphorus atom-containing group having 1 to 20 carbon atoms, provided that the R's may be the same or different and may be crosslinked to each other. Symbol a represents an integer of from 0 to 5.) In formula (1), the groups [$R_a$—Cp] (Cp represents η-cyclopentadienyl) may be the same or different.

The metallocene compound comprising a transition metal of Group VIII of the periodic table and aromatic electron system ligands is not particularly limited in its aromatic electron system ligands. Preferable examples of the ligands include π-arenes, indenyl, and η-cyclopentadienyl. Particularly preferred of these is η-cyclopentadienyl. Examples of substituents which may be bonded to each ligand include halogen atoms, hydrocarbon groups having 1 to 20 carbon atoms, halogenated hydrocarbon groups having 1 to 20 carbon atoms, and silicon atom-containing, oxygen atom-containing, sulfur atom-containing, and phosphorus atom-containing groups having 1 to 20 carbon atoms. Each ligand may have the same or different substituents, and the substituents may be crosslinked to each other.

Preferable transition metals for the metallocene compound comprising a transition metal of Group VIII of the periodic table and aromatic electron system ligands include iron, osmium, ruthenium, cobalt and nickel. Examples of the metallocene compound comprising a transition metal of Group VIII of the periodic table and aromatic electron system ligands for use in the present invention are shown below. These compounds may be used either alone or as a mixture of two or more thereof.

(e) Examples of compounds having one or more halogen atom substituents include 4-acetyl-1'-bromo-1,2-diethylferrocene, 1'-bromo-1,2,3-triethylferrocene, 1-acetyl-1'-bromo-2,3-diethylferrocene, 1-iodo-1'-(4-methoxyphenyl)ferrocene, and 1-bromo-1'-(ethoxycarbonyl)ferrocene.

(f) Examples of compounds having one or more hydrocarbon group substituents having 1 to 20 carbon atoms include 1,1'-dimethylferrocene, 1,1'-di-n-butylferrocene, bis(pentamethylcyclopentadienyl)iron, 1,1'-diethylferrocene, 1,1-dipropylferrocene, 1,1'-di-n-pentylferrocene, 1,1'-di-n-hexylferrocene, 1,1',2-trimethylferrocene, 1,1',2-triethylferrocene, 1,1',2-tripropylferrocene, 1,1',2-tri-n-butylferrocene, 1,1',2-tri-n-pentylferrocene, 1,1',2-tri-n-hexylferrocene, 1,1',3-trimethylferrocene, 1,1',3-triethylferrocene, 1,1',3-tripropylferrocene, 1,1',3-tri-n-butylferrocene, 1,1',3-tri-n-pentylferrocene, 1,1',3-tri-n-hexylferrocene, 1,1',2,3'-tetramethylferrocene, 1,1',2,3'-tetraethylferrocene, 1,1',2,3'-tetrapropylferrocene, and 1,1',2,3'-tetra-n-butylferrocene.

(g) Examples of compounds having one or more halogenated hydrocarbon group substituents having 1 to 20 carbon atoms include 1-methyl-1'-(chloromethyl)ferrocene, 1-chloro- 1'-(chloromethyl)ferrocene, 1-methyl-1'-(bromomethyl)ferrocene, 1-methyl-1'-(iodomethyl) ferrocene, 1,1'-di(chloromethyl)ferrocene, 1,1',2-tri (chloromethyl)ferrocene, 1,1',2,2'-tetra(chloromethyl) ferrocene, bis(pentachloromethylcyclopentadienyl)iron, and bis(pentabromomethylcyclopentadienyl)iron.

(h) Examples of compounds having one or more silicon atom-containing group substituents having 1 to 20 carbon atoms include 1-methyl-1'-(trimethylsilylmethyl)ferrocene, 1-methyl-1'-(trimethylsilylethyl)ferrocene, 1-methyl-1'-(trimethylsilylpropyl)ferrocene, 1,1'-di(trimethylsilylmethyl)ferrocene, 1,1'-di(trimethylsilylethyl) ferrocene, 1,1'-di(dimethylsilylmethyl)ferrocene, 1-acetyl-1'-(trimethylsilylmethyl)ferrocene, 1,1'-diacetyl-2-(trimethylsilylmethyl)ferrocene, and 1,1'-diacetyl-3-(trimethylsilylmethyl)ferrocene.

(i) Examples of compounds having one or more oxygen atom-containing group substituents having 1 to 20 carbon atoms include 1,1'-di(acetylcyclopentadienyl)iron, 1,1'-dibenzoylferrocene, 1,1'-bis(1-oxonyl)ferrocene, 1,1'-bis(1-oxooctadecyl)ferrocene, 1,1'-bis(1-oxohexyl)ferrocene, 1-acetyl-1'-ethynylferrocene, ferrocenyl vinyl ketone, ferrocenylmethyl methacrylate, and ferrocenyl vinyl ether.

(j) Examples of compounds having one or more sulfur atom-containing group substituents having 1 to 20 carbon atoms include 1,1'-bis(4-mercapto-1-oxobutyl)ferrocene, 1-(2-phenylethyl)- 1'-(2-thienylcarbonyl)ferrocene, 1-ethyl-3-(1-hydroxyethyl)-1'-(2-thienylcarbonyl)ferrocene, 1-(phenylacetyl)-1'-(2-thienylcarbonyl)ferrocene, 1-benzoyl-1'-(2-thienylcarbonyl)ferrocene, 1-acetyl-1'-(methoxysulfonyl)ferrocene, and 1-acetyl-1'-sulfoferrocene.

(k) Examples of compounds having one or more phosphorus atom-containing group substituents having 1 to 20 carbon atoms include 1,1'-bis(diphenylphosphino)ferrocene, 1-acetyl-1'-((diphenylphosphino)acetyl)ferrocene, 1,1'-bis( (diphenylphosphino)acetyl)ferrocene, 1-(diphenylphosphino)-1'-formylferrocene, 1-acetyl-1'-(diphenylphosphino)ferrocene, and 1-acetyl-1'-(diphenylphosphinyl)ferrocene.

(l) Examples of compounds having substituents crosslinked to each other include 1,1'-diacetyl-2,3'-(1,3-propanediyl)ferrocene, 1,2-diacetyl-1,4'-(1,4-butanediyl) ferrocene, 1,1'-bis(methoxycarbonyl)-2,2'-(oxybis (methylene))ferrocene, and 1,1'-bis(ethoxycarbonyl)-2,2'-(oxybis(methylene))ferrocene.

In the mixed catalyst (b) for use in the present invention, which consists of a combination of a cleavage-type photoinitiator (accelerator) and a metallocene compound comprising a transition metal of Group VIII of the periodic table and aromatic electron system ligands, the metallocene compound comprising a transition metal of Group VIII of the periodic table and aromatic electron system ligands is the same as described above with regard to (a). Examples of the cleavage-type photoinitiator include the photoinitiators enumerated below under (i) to (iii). These photoinitiators may be used either alone or as a mixture of two or more thereof.

(i) Examples of acetophenone photoinitiators include 4-phenoxydichloroacetophenone, 4-t-butyldichloroacetophenone, 4-t-butyltrichloroacetophenone, diethoxyacetophenone, 2-hydroxy-2-methyl-1-phenylpropan-1-one, 1-(4-isopropylphenyl)-2-hydroxy-2-methylpropan-1-one, 1-(4-dodecylphenyl)-2-hydroxy-2-methylpropan-1-one, 4-(2-hydroxyethoxy)phenyl (2-hydroxy-2-propyl) ketone, 1-hydroxycyclohexyl phenyl ketone, and 2-methyl-1-(4-(methylthio)phenyl)-2-morpholinopropane-1.

(ii) Examples of benzoin photoinitiators include benzoin, benzoin methyl ether, benzoin ethyl ether, benzoin isopropyl ether, benzoin isobutyl ether, and benzoin methyl ketal.

(iii) Examples of other photoinitiators include α-acyloxime esters, acylphosphine oxides, methylphenyl glyoxylate, 3,3',4,4'-tetra(t-butyl peroxycarbonyl) benzophenone, and 2,2'-azobis(2-methylbutyronitrile).

Examples of the acetylacetonatoplatinum(II) complex for use in imparting photocurability to a cyanoacrylate adhesive composition include Pt(acac)$_2$.

Examples of the specific metal complex releasing a nucleophilic agent upon light irradiation which is usable for imparting photocurability to a cyanoacrylate adhesive composition include the following compounds:

trans-[Cr(NH$_2$)$_2$(NCS)$_4$]$^-$
trans-[Cr(en)$_2$(NCS)$_2$]$^+$
trans-[Co(en)$_2$Cl$_2$]$^+$
trans-[Cr(cyclam)Cl$_2$]$^+$
trans-[Cr(cyclam)(NCS)$_2$]$^+$
trans-[Co(cyclam)Cl$_2$]$^+$ wherein en represents ethylenediamine and cyclam represents 1,4,8,11-tetraazacyclotetradecane.

The mixing ratio of the photocurable cyanoacrylate adhesive composition of the present invention and the above described catalyst is not particularly limited as long as the amount of the catalyst is enough to photopolymerize the cyanoacrylate monomer. For example, in the case of using (a) the metallocene compound comprising a transition metal of Group VIII of the periodic table and aromatic electron system ligands, the metallocene compound is added in an amount of 10 to 100,000 ppm by weight, preferably 30 to 50,000 ppm by weight based on the weight of the cyanoacrylate monomer. In the case of using (b) cleavage-type photoinitiator, the photoinitiator is added, in general, in an amount of 100 to 20,000 ppm by weight, preferably 300 to 15,000 ppm by weight based on the weight of the cyanoacrylate monomer, although the suitable addition amount varies depending on kinds and the addition amount of the metallocene compound.

The photocurable cyanoacrylate adhesive composition for use in the present invention may be used in combination with a radical-polymerizable compound such as acrylate ester. Furthermore, the photocurable cyanoacrylate adhesive composition may, if necessary, further contain one or more of known specific additives such as anionic-polymerization inhibitors, radical-polymerization inhibitors, thickening agents, curing accelerators, plasticizers, tougheners, perfumes, dyes, pigments, fillers, and heat stabilizers.

A radical-polymerizable compound such as an acrylic ester, can be added to the photocurable composition of the present invention. Even if a radical-polymerizable compound is added, the photocurable composition of the present invention can be rapidly cured owing to the cleavage-type photoinitiator.

An anionic-polymerization inhibitor may be added in order to enhance the storage stability of the composition. Known examples thereof include sulfur dioxide, sulfur trioxide, nitrogen oxide, hydrogen fluoride, and p-toluenesulfonic acid. The anionic-polymerization inhibitor may be added in an amount of 0.1 to 10,000 ppm by weight based on the weight of the α-cyanoacrylate.

Examples of radical-polymerization inhibitors include quinone, hydroquinone, t-butylcatechol, and p-methoxyphenol. The radical-polymerization inhibitor may be added in an amount of 0.1 to 10,000 ppm by weight based on the weight of the α-cyanoacrylate.

A thickening agents may be added in order to heighten the viscosity of the composition. Examples thereof include poly(methyl methacrylate), methacrylate copolymers, acrylic rubbers, cellulose derivatives, poly(vinyl acetate), and poly(α-cyanoacrylate)s.

Many kinds of polymeric additives may be added usually for toughening. Examples thereof include acrylic elastomers, acrylonitrile copolymer elastomers, fluoroelastomers, and a fine silica filler. These substances function also as thickening agents.

EXAMPLES

The present invention will be explained below by reference to Examples and Comparative Examples, but the invention should not be construed as being limited to these Examples. The parts as used in the Examples and Comparative Examples and values as used in the table are by weight unless otherwise specified.

In the Examples and Comparative Examples, Three Bond 1743 (product of Three Bond Co., Ltd.; main component: ethyl α-cyanoacrylate; hereinafter abbreviated as TB1743) was used as an α-cyanoacrylate.

For the evaluation of photocurability, a 4-kw high-pressure mercury lamp (manufactured by ORC Manufacturing Co., Ltd.) was used as an ultraviolet irradiator. The photocurability of each of the compositions was evaluated by placing 1 g of a sample in a polyethylene tray with an inner diameter of 30 mm and irradiating the sample with light from a distance of 15 cm to measure the integrated quantity of light needed for curing. The results of a photocurability test shown in the Examples and Comparative Examples are given in terms of the integral of the quantity of light needed for complete photocuring.

The following abbreviations are used in the following Examples and Comparative Example.
Transition metal metallocene compounds:

| | |
|---|---|
| Ferrocene | Cp$_2$Fe |
| 1,1'-Diacetylferrocene | (AcCp)$_2$Fe |
| Bis(pentamethylcyclopentadienyl)osmium | (Me$_5$Cp)$_2$Os |
| Ruthenocene | Cp$_2$Ru |
| Cleavage-type photoinitiator: | |
| Acylphosphine oxide | APO |
| Irgacure 184 (Ciba-Geigy Ltd.) | Irg184 |

TABLE 1

| | Ex. 1 | Ex. 2 | Ex. 3 | Ex. 4 | Ex. 5 | Ex. 6 | Comp. Ex. 1 |
|---|---|---|---|---|---|---|---|
| TB1743 | 100 | 100 | 100 | 100 | 100 | 100 | 100 |
| Cp$_2$Fe | 5 | | | | 0.5 | 0.5 | |
| (AcCp)$_2$Fe | | 0.1 | | | | | |
| (Me$_5$Cp)$_2$Os | | | 0.1 | | | | |
| Cp$_2$Ru | | | | 0.01 | | | |
| APO | | | | | 0.1 | | |
| Irg184 | | | | | | 1 | |
| Photocurability | 2000 | 1000 | 1000 | 2000 | 1000 | 2000 | 30000< |

Examples 1 to 4

Samples each consisting of TB1743 and any of various transition metal metallocene compounds were prepared according to formulations shown in Table 1 as follows. A hundred grams of TB1743 was placed in a 200-ml beaker, and the contents were stirred with Three-One Motor at 300 rpm. Thereto was added the given amount of each of the transition metal metallocene compounds little by little. Each resulting mixture was continuously stirred at room temperature for 1 hour to dissolve the metallocene compound. These samples were prepared in a dark room, and were stored in light-shielded containers.

Examples 5 and 6

Samples each consisting of TB1743, Cp$_2$Fe, and a cleavage-type photoinitiator were prepared according to formulations shown in Table 1 as follows. A hundred grams of TB1743 was placed in a 200-ml beaker, and the contents were stirred with Three-One Motor at 300 rpm. A cleavage-type photoinitiator was added thereto and dissolved with stirring. In the case where the cleavage-type photoinitiator was APO, it was dissolved by stirring the mixture first at 50° C. for 8 hours and then at room temperature overnight. In the case where the cleavage-type photoinitiator was Irg184, it was dissolved by stirring the mixture at room temperature for 1 hour. Subsequently, the given amount of $Cp_2Fe$ was added to each solution little by little, and was dissolved by continuously stirring each resulting mixture at room temperature for 1 hour. These samples were prepared in a dark room, and were stored in light-shielded containers.

Comparative Example 1

As a comparative example, results of the evaluation of TB1743 alone are shown.

Subsequently, each of the adhesive compositions shown in Examples 1 to 6 and Comparative Example 1 was used for the bonding of an artificial nail (product of Lee Pharmaceuticals Co., U.S.A.) to a nail to measure the curing time. Each adhesive composition was further evaluated for suitability for the building up of the adhesive at the joint between the nail and the artificial nail as follows. Each adhesive composition was applied to the joint between the nail and artificial nail, and the applied composition was irradiated with light to measure the time required for the adhesive to cure. As light sources were used a 100-W high-pressure mercury lamp spot irradiator (QRU-2266, manufactured by Oak Manufacturing Co., Ltd.) and a metal halide illuminant spot irradiator having an illuminance of 1,400,000 1× (ML60, manufactured by HOYA-SCHOTT Co.). The results obtained are shown in Table 2.

TABLE 2

|  | Ex. 1 | Ex. 2 | Ex. 3 | Ex.4 | Ex. 5 | Ex. 6 | Comp. Ex. 1 |
|---|---|---|---|---|---|---|---|
| Nail/artificial nail banding time (sec) | 5–10 | 5–10 | 5–10 | 5–10 | 5–10 | 5–10 | 5–10 |
| Curing time in joint filling (sec) High-pressure mercury lamp | 15 | 10 | 10 | 15 | 10 | 15 | uncured in 300 |
| Metal halide illuminant | 90 | 60 | 60 | 70 | 60 | 70 | uncured in 300 |

Table 2 shows that the photocurable α-cyanoacrylate adhesives according to the present invention had the same nail/artificial nail bonding performance as the conventional α-cyanoacrylate adhesive and were capable of being rapidly cured by light irradiation. Therefore, the adhesives according to the present invention can also be used not only for the filling (or building up) of the recessed part of the a nail/artificial nail joint but as a coating agent for finishing or as an adhesive for bonding a decorative article for an artificial nail, for which the conventional α-cyanoacrylate adhesive has been unusable.

The photocurable cyanoacrylate adhesive according to the present invention applied for bonding a nail to an artificial nail or for bonding a decorative article to a nail or artificial nail can be cured speedily even when it has been applied thickly (for building up) or has flowed out of the bonding part, in which case conventional cyanoacrylate adhesives require much time for curing. This is because the adhesive according to the present invention which has been applied in such a manner that rapid curing is difficult for conventional cyanoacrylate adhesives can be cured in an extremely short time period by irradiation with light. The photocurable cyanoacrylate adhesive according to the present invention has an excellent effect that it is usable not only as an adhesive for nail/artificial nail bonding, but also for the filling (or building up) of the recessed part of a nail/artificial nail joint, as a coating agent for finishing, or as an adhesive for bonding a decorative article to an artificial nail, while retaining the excellent features of the instantaneous adhesive, i.e., cold-setting and single-liquid type. Due to the above, the whole process for artificial-nail attachment beginning with the bonding of an artificial nail and ending with finishing can be carried out with only one α-cyanoacrylate adhesive, in contrast to the conventional process for artificial-nail attachment in which two or more adhesives should be used according to uses. As a result, the troublesomeness of artificial-nail attachment can be eliminated and the efficiency of the procedure can be greatly improved.

While the invention has been described in detail and with reference to specific embodiments thereof, it will be apparent to one skilled in the art that various changes and modifications can be made therein without departing from the spirit and scope thereof.

What is claimed is:

1. A method of bonding an artificial nail to a nail with an adhesive or of bonding a decorative article to an artificial nail or a nail using an adhesive, said adhesive being a photocurable cyanoacrylate adhesive, said method comprising applying said adhesive to a bonding surface of at least one adherend selected from the group consisting of a nail, an artificial nail and a decorative article, subsequently superposing a plurality of the adherends on each other, and then irradiating said superposed adherends with light to cure the adhesive and complete the bonding.

2. The method of bonding an artificial nail to a nail with an adhesive or of bonding a decorative article to an artificial nail or a nail using an adhesive as claimed in claim 1, wherein the photocurable cyanoacrylate adhesive comprises:

(A) an α-cyanoacrylate and
   (B) a metallocene compound comprising a transition metal of Group VIII of the periodic table and aromatic electron system ligands.

3. The method of bonding an artificial nail to a nail with an adhesive or of bonding a decorative article to an artificial nail or a nail using an adhesive as claimed in claim 2, wherein each of the aromatic electron system ligands in the metallocene compound (B) is a π-arene, indenyl, or η-cyclopentadienyl.

4. The method of bonding an artificial nail to a nail with an adhesive or of bonding a decorative article to an artificial nail or a nail using an adhesive as claimed in claim 2, wherein the metallocene compound (B) comprising a transition metal of Group VIII of the periodic table and aromatic electron system ligands is represented by the following formula (1):

(wherein M represents a transition metal of Group VIII of the periodic table; R represents a halogen atom, a hydrocarbon group having 1 to 20 carbon atoms, a halogenated hydrocarbon group having 1 to 20 carbon atoms, or a silicon-atom containing, oxygen-atom containing, sulfur-atom containing, or phosphorus-atom containing group having 1 to 20 carbon atoms, provided that the R's may be the same or different and may be crosslinked to each other; symbol a represents an integer of from 0 to 5; and the groups [R$_a$—Cp] (Cp represents η-cyclopentadienyl) may be the same or different).

5. The method of bonding an artificial nail to a nail with an adhesive or of bonding a decorative article to an artificial nail or a nail using an adhesive as claimed in claim 2, wherein the transition metal of Group VIII of the periodic table in the metallocene compound (B) is a transition metal selected from the group consisting of iron, osmium, ruthenium, cobalt and nickel.

6. The method of bonding an artificial nail to a nail with an adhesive or of bonding a decorative article to an artificial nail or a nail using an adhesive as claimed in claim 3, wherein the photocurable cyanoacrylate adhesive further comprises (C) a cleavage means for photoinitiating.

7. The method of bonding an artificial nail to a nail with an adhesive or of bonding a decorative article to an artificial nail or a nail using an adhesive as claimed in claim 6, wherein each of the aromatic electron system ligands in the metallocene compound (B) is a π-arene, indenyl, or η-cyclopentadienyl.

8. The method of bonding an artificial nail to a nail with an adhesive or of bonding a decorative article to an artificial nail or a nail using an adhesive as claimed in claim 6, wherein the metallocene compound (B) comprising a transition metal of Group VIII of the periodic table and aromatic electron system ligands is represented by the following formula (1):

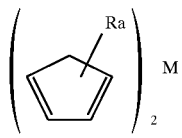

(wherein M represents a transition metal of Group VIII of the periodic table; R represents a halogen atom, a hydrocarbon group having 1 to 20 carbon atoms, a halogenated hydrocarbon group having 1 to 20 carbon atoms, or a silicon-atom containing, oxygen-atom containing, sulfur-atom containing, or phosphorus-atom containing group having 1 to 20 carbon atoms, provided that the R's may be the same or different and may be crosslinked to each other; symbol a represents an integer of from 0 to 5; and the groups (R$_a$—Cp] (Cp represents η-cyclopentadienyl) may be the same or different).

9. The method of bonding an artificial nail to a nail with an adhesive or of bonding a decorative article to an artificial nail or a nail using an adhesive as claimed in claim 6, wherein the transition metal of Group VIII of the periodic table in the metallocene compound (B) is a transition metal selected from the group consisting of iron, osmium, ruthenium, cobalt and nickel.

10. The method of bonding an artificial nail to a nail with an adhesive or of bonding a decorative article to an artificial nail or a nail using an adhesive as claimed in claim 1, wherein the photocurable cyanoacrylate adhesive comprises:

(A) an α-cyanoacrylate and (B) an acetylacetonatoplatinum(II) complex.

11. The method of bonding an artificial nail to a nail with an adhesive or of bonding a decorative article to an artificial nail or a nail using an adhesive as claimed in claim 1, wherein the photocurable cyanoacrylate adhesive comprises:

(A) an α-cyanoacrylate and (B) a metal complex which releases a nucleophilic agent upon light irradiation.

12. The method of bonding an artificial nail to a nail with an adhesive or of bonding a decorative article to an artificial nail or a nail using an adhesive as claimed in claim 6, wherein the means for photoinitiating comprises a cleavage photoinitiator selected from the group consisting of acetophenone photoinitiators and benzoin photoinitiators.

13. The method of bonding an artificial nail to a nail with an adhesive or of bonding a decorative article to an artificial nail or a nail using an adhesive as claimed in claim 12, wherein the means for photoinitiating comprises an acetophenone photoinitiator selected from the group consisting of 4-phenoxydichloroacetophenone, 4-t-butyldichloroacetophenone, 4-t-butyltrichloroacetophenone, diethoxyacetophenone, 2-hydroxy-2-methyl-1-phenylpropan-1-one, 1-(4-isopropylphenyl)-2-hydroxy-2-methylpropan-1-one, 1-(4-dodecylphenyl)-2-hydroxy-2-methylpropan-1-one, 4-(2-hydroxyethoxy)phenyl (2-hydroxy-2-propyl) ketone, 1-hydroxycyclohexyl phenyl ketone and 2-methyl-1-(4-(methylthio)phenyl)-2-morpholinopropane.

14. The method of bonding an artificial nail to a nail with an adhesive or of bonding a decorative article to an artificial nail or a nail using an adhesive as claimed in claim 12, wherein the means for photoinitiating comprises a benzoin photoinitiator selected from the group consisting of benzoin, benzoin methyl ether, benzoin ethyl ether, benzoin isopropyl ether, benzoin isobutyl ether and benzoin methyl ketal.

15. The method of bonding an artificial nail to a nail with an adhesive or of bonding a decorative article to an artificial nail or a nail using an adhesive as claimed in claim 6, wherein the means for photoinitiating comprises a cleavge photoinitiator selected from the group consisting of acyloxime esters, acylphosphine oxides, methylphenyl glyoxylate, 3,3',4,4'-tetra(t-butyl peroxycarbonyl) benzophenone and 2,2'-azobis(2-methylbutyronitrile).

* * * * *